United States Patent [19]

Chang

[11] Patent Number: 4,469,562
[45] Date of Patent: Sep. 4, 1984

[54] CARBON DIOXIDE SENSOR

[76] Inventor: Kuo-Wei Chang, 32 Buckman Dr., Lexington, Mass. 02173

[21] Appl. No.: 454,421

[22] Filed: Dec. 29, 1982

[51] Int. Cl.³ ............................................ G01N 27/46
[52] U.S. Cl. .................................. 204/1 T; 204/403; 204/415
[58] Field of Search ............... 204/1 T, 1 K, 403, 406, 204/415, 431, 432, 433; 429/30, 33, 41

[56] References Cited

U.S. PATENT DOCUMENTS

| | | | |
|---|---|---|---|
| 3,382,105 | 5/1968 | McBryer et al. | 429/30 |
| 4,049,503 | 9/1977 | Becker et al. | 204/406 |
| 4,263,115 | 4/1981 | Kessler et al. | 204/415 |
| 4,377,446 | 3/1983 | Albery | 204/415 |

FOREIGN PATENT DOCUMENTS 1442303 7/1976 United Kingdom ................ 204/403

Primary Examiner—R. L. Andrews
Assistant Examiner—Terryence Chapman
Attorney, Agent, or Firm—Thompson, Birch Gauthier & Samuels

[57] ABSTRACT

An electrolyte anion exchange sensor having a first diffusion membrane is spaced apart from an anion exchange membrane to form a cathodic cell. A second diffusion membrane is spaced apart from the anion exchange to form an anodic cell. $CO_2$ flows through the first membrane and is ionized. The bicarbonate ions flow through the anion exchange membrane into the anodic compartment and reacts to form $CO_2$. The current change in the electrolyte path corresponds to the amount of $CO_2$.

10 Claims, 8 Drawing Figures

CARBON DIOXIDE SENSOR

BACKGROUND AND BRIEF SUMMARY OF THE INVENTION

The invention relates generally to an electrochemical cell used as a carbon dioxide sensor, and more particularly to an anion exchange cell for measuring carbon dioxide.

An electrochenmical cell, in simplest terms, consists of an anode (the oxidizing electrode), a cathode (the reducing electrode) and an electrolyte. In order for the electrochemical cell to function, the electrolyte must be compatible with the mechanisms of oxidation and reduction at the electrodes, and it must provide a conductive path for the transport of ionic species between the electrodes.

Electrochemical cells, due to their very high level of sensitivity, are used for measurement in a variety of analytical procedures and many laboratory and process control instruments depend upon the electrochemical cell as a sensor element.

Conventional carbon dioxide sensors use a pH probe to measure the concentration of the hydrogen ion produced when the carbon dioxide is hydrated. One sensor which has widespread acceptance is the Severinghaus carbon dioxide electrode which consists of a standard glass pH electrode covered with a Teflon membrane. Between the glass surface and the membrane exists a thin film of dilute sodium bicarbonate solution. After the carbon dioxide diffuses through the membrane the carbon dioxide becomes equilibrated with the electrolyte solution, the pH of the solution is measured by the glass electrode and it can be interpreted in terms of $pCO_2$ on the basis of the linear relationship between log $pCO_2$ and pH as described by the Henderson-Hasselbalch equation.

Although the Severinghaus electrode has gained wide-spread acceptance it is not especially suitable in all instances. This is particularly true where it is desired to measure carbon dioxide content in a respiratory system such as in a diving application or in a biomedical application. Where the pH value is determined in terms of the potential developed by the glass pH electrode, the electrode has a very high internal impedance generally in excess of 200M ohms because the potential is generated by the diffusion of relatively few hydrogen ions across the insulating glass membrane. The glass pH probe is fragile and the electrodes are sensitive to temperature due to changes in properties of the glass membrame. Lastly, most carbon dioxide electrodes have a tendency to drift and frequent calibration is required. The present invention embodies a compact, stable, rugged carbon dioxide sensor suitable for underwater application.

Broadly, the invention is directed to an electrolytic anion exchange sensor based on a diffusion controlled current measurement to determine carbon dioxide content. More particularly, the invention is directed to causing the current to correspond to the diffusion flux of carbon dioxide molecules in an anion exchange cell.

Broadly, my invention comprises an anion exchange cell having a first diffusion membrane permeation selective for $CO_2$ and an anion exchange membrane spaced apart therefrom to define a cathodic compartment. The cathodic compartment contains a cathode and an electrolyte. A second diffusion membrane is spaced apart from the anion exchange membrane and defines therewith an anodic compartment. The anodic compartment contains an electrolyte and an anode. The carbon dioxide diffused through the first membrane is hydrated forming bicarbonate and hydrogen ions. The bicarbonate ions pass through the anion exchange membrane to the anode. Carbon dioxide is formed and diffuses through the second membrane. The current flowing between the electrodes is measured and this current corresponds to the amount of carbon dioxide in the fluid stream in communication with the cell.

DESCRIPTION OF THE PREFERRED EMBODIMENTS

My invention will be described in connection with the following examples which are intended to be illustrative and not limiting.

EXAMPLE I

Figure 1:
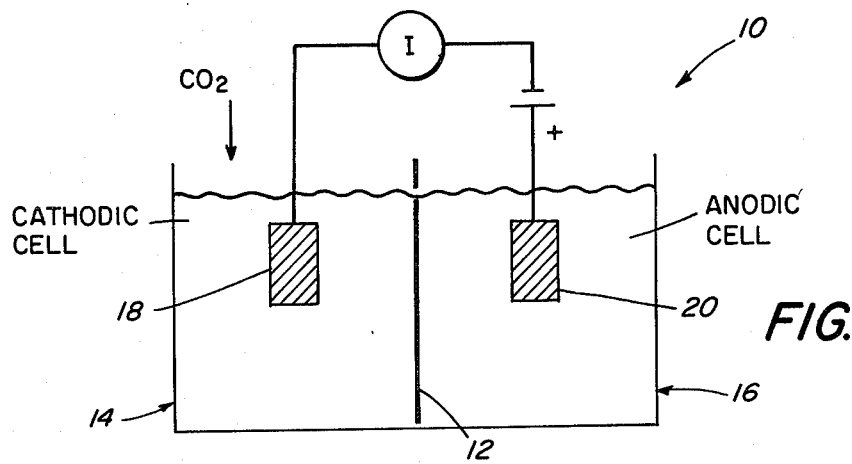
FIG. 1 is a schematic view of an anion exchange sensor.

A sensor 10, as shown in FIG. 1 was used and comprised an anion exchange membrane 12, manufactured by American Machine and Foundry Company of White Plains, NY (type A-100), interposed between two acrylic compartments 14 and 16 and two identical tantalum foil electrodes which functioned as a cathode 18 and an anode 20. The compartments 14 and 16 were individually filled with distilled water and no electrolyte whatsoever was added. Because potential measurements were to be avoided, a constant voltage was maintained between the electrodes 18 and 20 and the cell current was measured with a low input impedance (practically speaking, 0 ohm) amplifier. The electrodes were approximately 4 cm apart and were made up of 1 cm×5 cm tantalum foils (0.013 cm thick) with a tantalum wire spot-welded to one corner.

A 6-Volt battery 22 was used for electrode bias. After an initial surge, the cell current gradually decreased and eventually reached a steady state of value of approximately 7 A. This constant current was believed to be sustained by $H^+$ and $OH^-$ ions generated by the spontaneous ionization of $H_2O$.

After initial equilibration, 100% CO was bubbled slowly into the cathodic cell 14. The cell current increased rapidly, reaching a peak of approximately 250 A. After the gas was switched off, the current remained at the elevated level for hours and eventually it returned to roughly the original value. The $CO_2$ induced current is believed to be sustained by $H^+$ and $HCO^-$ ions.

Within the cathodic compartment, the reversible hydration of carbon dioxide occurs spontaneously:

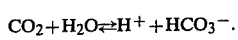

Some of the HCO ions undergo further ionization:

The $H^+$ ions formed are drawn to the cathode and subsequently effervesed as hydrogen gas. The anions HCO$_3^-$ and CO$_3^{--}$ are drawn through the anion exchange membrane and react at the anode to form O$_2$ and CO$_2$:

$$4HCO_3^- \rightarrow 4CO_2 + 2H_2O + O_2 + 4e$$

$$2CO_3^{--} \rightarrow 2CO_2 + O_2 + 4e.$$

The CO$_2$ gas released at the anode may very well be rehydrated to form H$^+$, HCO$_3^-$ and CO$_3^{--}$ ions within the anodic compartment. Because of the large potential gradient which exists across the anion exchange membrane 12, HCO$_3^-$ and CO$_3^{--}$ ions are prevented from returning to the cathodic compartment.

After completion of the previous test, the half cells were evacuated and replaced with fresh distilled water. Following initial equilibration, 100% CO$_2$ was introduced to the anodic cell 16 instead of the cathodic cell 14. The response of the test cell became entirely different. There was only an insignificant and gradual rise in the cell current (2 to 3 A). The small increase in the cell current is believed to be due to a slight increase in the conductivity of the water within the anodic compartment resulting from formation of H$^+$, HCO$_3^-$ and CO$_3^{--}$ ions.

It appears that in the test cell of Example I and FIG. 1, CO$_2$ is continuously transported across the anion exchange membrane in such a manner that the CO$_2$ flux is proportional to the cell current. Therefore, a CO$_2$ sensor was devised based on the test cell of FIG. 1. However, to function as a CO$_2$ sensor, a diffusion barrier must be provided so that the cell current can become CO$_2$ supply limited.

EXAMPLE II

Figure 2:
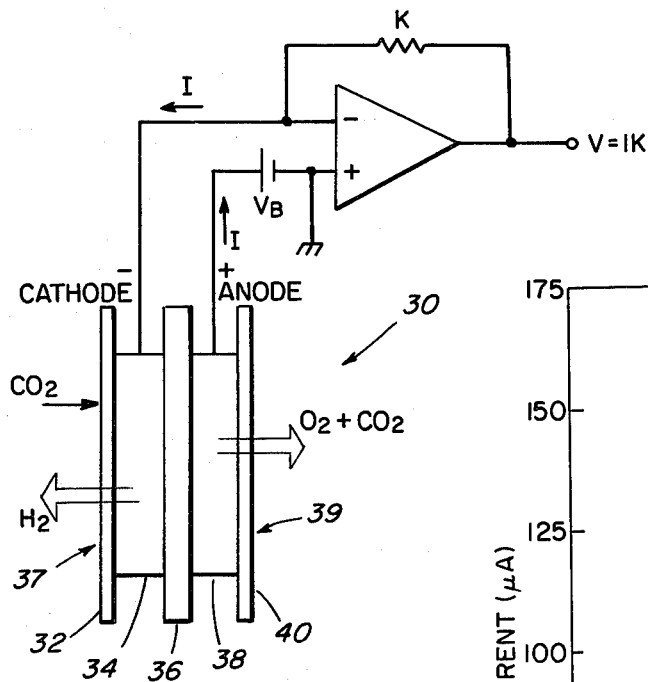
FIG. 2 is a schematic view of an anion exchange sensor embodying my invention.

An anion exchange sensor 30 is schematically shown in FIG. 2 with gaskets, retaining screens and protective separators omitted. Several sensors 30 were used in the tests but only one will be described. The sensor 30 was used in the following tests and comprised; a CO$_2$ diffusion membrane 32 (dimethyl silicone rubber, 0.0013 cm thick, General Electric Company, Schenectady, N.Y.); a cathode 34 (porous gold-black, Engelhard Industries, Carteret, N.J.); an anion exchange membrane 36, (A-100 exchange resin, American Machine and Foundry Company, White Plains, N.Y.); an anode 38 (porous gold-black, Englehard Industries, Carteret, N.J.); an exhaust membrane 40 (dimethyl silicone rubber, 0.0013 cm thick, General Elecric company, Schenectady, N.Y.); electrolyte (100 mg% solution of carbonic anhydrase enzyme, 100 mg enzyme in 100 cm of distilled water, Sigma Chemical Company, St. Louis, MO, catalog no. C7500) saturated the cathode 34 and the anode 38. The membrane 32, cathode 34, anion exchange membrane 36 and the electrolyte formed a cathodic compartment 37. The membrane 40, anode 38, anion exchange membrane 36 and the electrolyte formed a anodic compartment 39. Carbon dioxide-% in air was passed through the diffusion membrane 32, CO$_2$ molecules immediately dissolved in the electrolyte and were subsequently hydrated through the reversible catalytic action of the carbonic anhydrase enzyme. The enzymatic reaction is believed to be as follows:

$$CO_2 + H_2O \underset{}{\overset{enzyme}{\rightleftharpoons}} HCO_3^- + H^+$$

As reported, the molecular weight of the enzyme is approximately 30,000, whereas the reaction rate is on the order of 620,000 CO$_2$ molecules hydrated per enzyme molecule per second.

The H$^+$ ions generated were drawn to the cathode 34 electrostatically to effervesce as hydrogen gas. On the other hand, the HCO$_3^-$ anions were drawn through the anion exchange membrane 36 and reacted at the anode 38 to form CO$_2$ and O$_2$. The reaction products O$_2$ and CO$_2$ are discharged by diffusion through the exhaust membrane 40.

Some of the CO$_2$ may rehydrate and remain in the anodic compartment 37. The anion exchange membrane 36 allows passage of HCO$_3^-$ ions but prevents CO$_2$ gas from returning to the sensing cathodic compartment 37. The backward migration of HCO$_3^-$ ions is prevented by the large potential gradient which exists across the anion exchange membrane 36.

Because the enzymatic hydration reaction is extremely fast, the diffusion transport of CO$_2$ molecules can become the rate determining step. As a result, the cell current becomes CO$_2$ diffusion-limited and is, therefore, linearly proportional to the partial pressure of carbon dioxide outside the sensor.

The sensor 30 was assembled in a layer-by-layer fashion using simple jigs and fixtures. The various layers were held together by two stainless steel end plates (not shown) and clamping screws. The active area of the sensor, which is determined by the openings in the end plates and the diameter of the cathode, was roughly 0.25 cm in diameter. The various layers in FIG. 2 (with the exception of the cathode an the anode) were 0.8 cm in diameter, whereas the end clamping plates were 1.9 cm in diameter. The cathode and the anode were presoaked in the enzyme solution and were kept wet all through the assembly procedure. The electrode lead wires consisted of Teflon coated gold wire 0.013 cm in diameter, which were stripped and pressed against the cathode and the anode, respectively. After assembly, the sensor was rinsed in distilled water to remove traces of enzyme solution external to the sensor.

Gaskets used for sealing were composed of polyethylene disks and rings. The fragile diffusion membranes were protected by thin sheets of hydrophobic, microporous polypropylene material. The overall thickness of the sensor was less than 0.4 cm.

After initial equilibration, the sensors was tested in a carbon-dioxide/helium test system-% CO$_2$ composed of flowmeters, check valves, flow restrictors and mixing valves. The electrode bias was provided by a variable voltage power supply at a setting of 2 Volts. The sensor current was monitored by a current amplifier with a front-end current-to-voltage convertor identical to that of FIG. 1. The test results of a typical sensor are presented in FIG. 3. The current corresponding to zero pCO$_2$ was 0.9 A and the sensor deviated from a linear response for pCO$_2$ values above 200 Torr. The sensor current became saturated for pCO$_2$ above 400 Torr., approximately.

Figure 4:
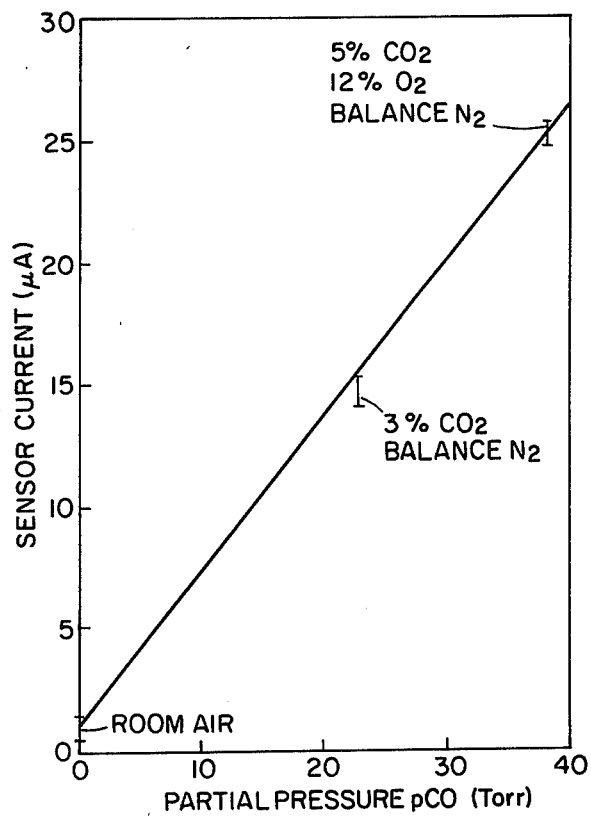
FIGS. 4-7 are graphs illustrating various results found with my inventive sensor; and, FIG. 8 is a schematic view of a three-electrode anion exchange sensor.

Sensors 30 have also been tested with premixed calibration gases. The data shown in FIG. 4 were obtained with the use of room air and calibration gases bottled by The London Company of Cleveland, Ohio. (5% CO$_2$, 12% O$_2$ balance N$_2$. The response time of the sensor has been measured by switching from room air to the premixed gas containing CO$_2$, and then back to room air after a steady state is reached. The characteristic response time, defined as the time to reach 63% of the steady state value, was found to be 5 seconds for increasing p$CO_2$ and 6 seconds for decreasing p$CO_2$, FIG. 5.

Figure 6:
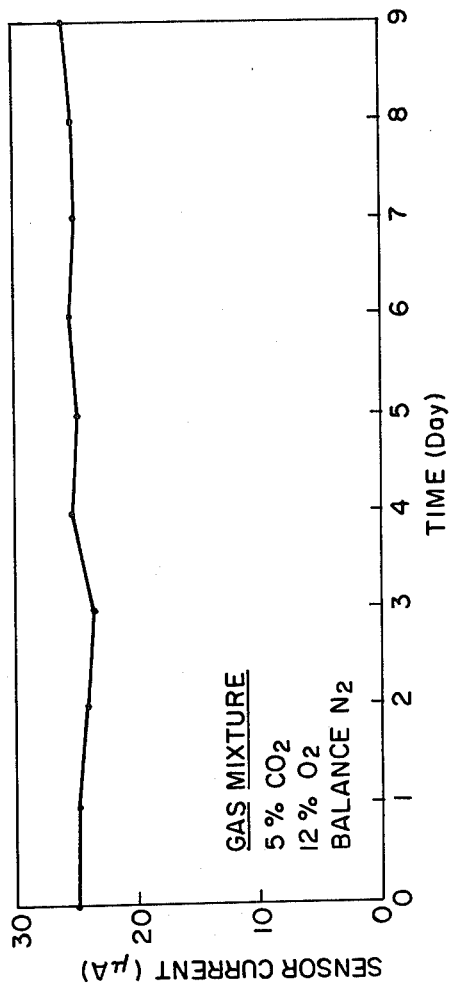

The long term stability of the p$CO_2$ sensor has been evaluated. The sensor was tested once a day for nine (9) days with the calibration gas. The sensor did not show any definite trend of upward or downward drift, however, it did show slight daily variations, FIG. 6. The sensor was continuously biased during the long term study and it was constantly wrapped in a wet towel to keep it from drying out.

Figure 3:
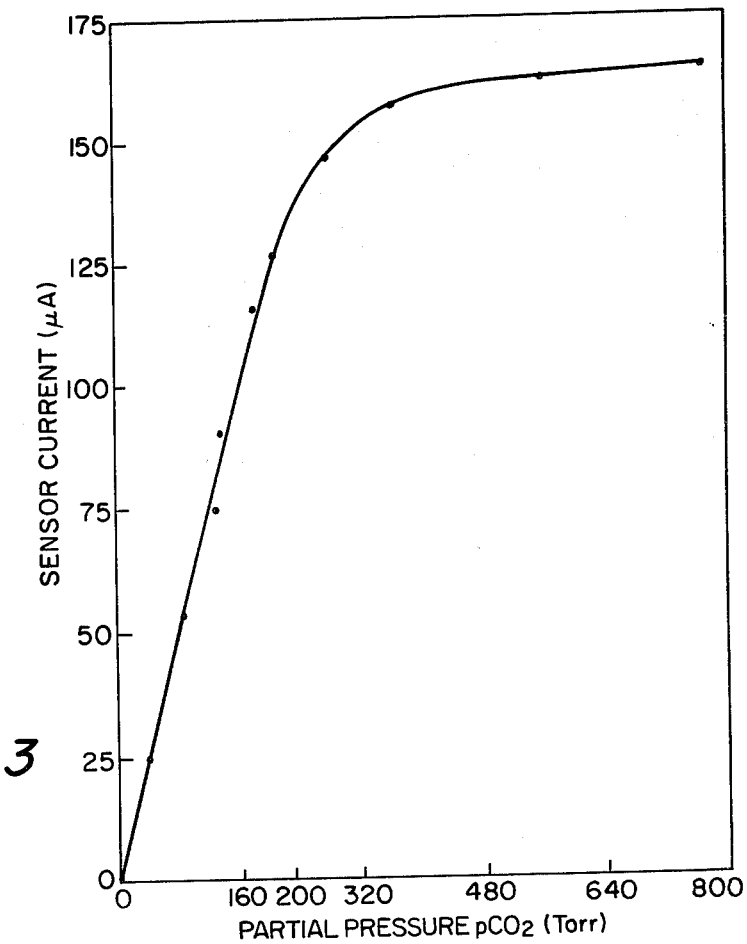

Based on the above results the sensor current was found to be linear with respect to p$CO_2$ only for values below 200 Torr. FIG. 3. In diving as well as in most biomedical applications, the p$CO_2$ range of interest rarely exceeds 100 Torr. Nevertheless, the reason for signal saturation was explored. Insufficient enzyme activity as the cause of saturation was ruled out because the linearity range of sensors constructed of different enzyme concentrations has been similar.

The reason for saturation was found to be due to insufficient voltage bias. At high concentrations of $CO_2$, the cell current becomes so large that only a portion the ions can be collected. It was found that operating the sensor at 6 Volts bias (instead of 2 Volts) extended the linear range to 450 Torr. approximately. However, the sensor degraded rapidly and the anion exchange membrane changed from the normal brown color into a black color. It appears that the high current density encountered at high p$CO_2$ had exceeded the performance limit of the anion exchange membrane.

Therefore, the sensor can be rendered linear over a wider dynamic range only by using a diffusion barrier less permeable to $CO_2$. The penalty for such an approach lies in a lengthening of the response time. However, the lack of linearity at high p$CO_2$ does not in any way detract from the usefulness and attractiveness of the sensor in diving as well as in biomedical applications.

In theory, when the potential of the cathode reaches the level of oxygen reduction potential (0.4 Volt in basic solution and 1.23 Volt in acidic solution, relative to standard hydrogen electrode), a current due to electrochemical reduction of $O_2$ to hydroxyl ion can occur. With the sensor 30 used to obtain the data the low sensitivity to oxygen can be attributed to the following factors:

(a) For the dimethyl silicone rubber membrane used, the permeability coeficient of $O_2$ is 5.4 times smaller than that of $CO_2$.

(b) The bulk of the potential drop was due to the anode, distilled water, and the anion exchange membrane so that the potential impressed on the cathode is relatively small.

(c) Within the pores of the cathode, the solution tends to be acidic due to the presence of $H^+$ resulting from $CO_2$ hydration. As a result, a higher potential is needed for oxygen reduction.

Gold-black is a superior electrode catalyst for $O_2$ reduction. The choice of porous gold-black as the anode material in the present p$CO_2$ sensor was largely due to non-availability of other more suitable materials. It is possible that materials. such as tantalum, cadmium, nickel, chromium and tungsten, can be used as a cathode in order to further reduce the oxygen sensitivity. Tantalum screen and foil was found to be unsuitable as an anode material. Rapid degradation perhaps due to the oxidation effect of $OH$ ions, had rendered the sensor insensitive to p$CO_2$ in a few days when a tantalum anode was used.

Commercial preparations of the carbonic anhydrase enzyme are known to be stable for more than a year at 5° C. Data on its stability at other temperatures have not been found in the literature. Because the enzyme is an animal (or plant) protein, addition of noninhibiting fungicide/bactericide may be required. On the other hand, the growth problem may be non-existent due to the low pH values encountered. Alternatively, the sensor interior may be sterilized by subjecting to 100% CO (i.e., low pH) initially (at open circuit to avoid large current surge).

Figure 7:
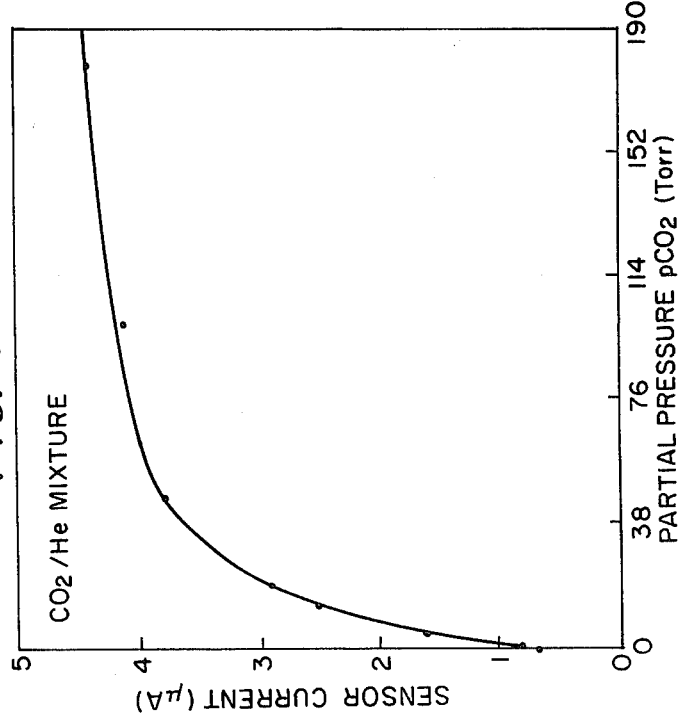

Sensors as shown in FIG. 2 without enzyme have also been constructed and investigated. The variation of sensor current with p$CO_2$ is shown in FIG. 7. As expected, the cell current is considerably smaller.

In addition to the slight sensitivity to oxygen, the p$CO_2$ sensor has a small but non-vanishing current at zero p$CO_2$. This offset current is due to impurity in the solution, and more importantly, due to the spontaneous ionization of $H_2O$ molecules. In 100% Helium, this offset current is less than 1 $\mu$A.

Because water is being consumed, the life span of the sensor is not unlimited. Based on water consumption calculations, the service life of the sensor was estimated to be 10 to 20 days for continuous operation at a p$CO_2$ level of 40 Torr; The life of the sensor can be extended by using a less permeable diffusion membrane.

Figure 5:
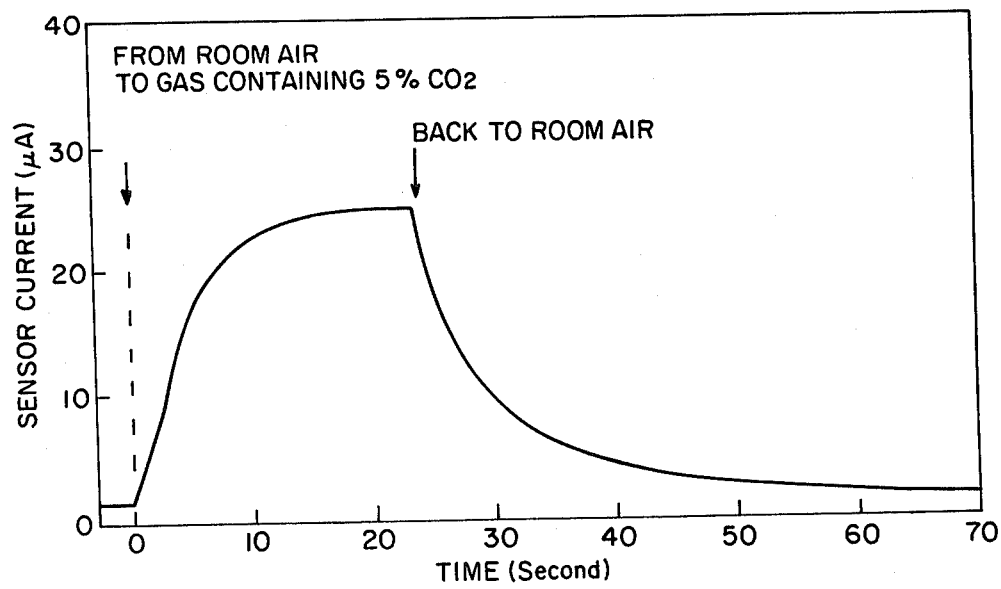

The response time of the p$CO_2$ sensor was typically on the order of 5 seconds (FIG. 5). A sensor of this performance can be used in a rebreather type SCUBA system to warn of dangerous elevations of the $CO_2$ concentration.

In that the sensor directly responds to p$CO_2$, it is readily operable under water with the same calibration as at sea level. Both sides of the sensor can be exposed to the same gas medium to be monitored.

The $CO_2$ sensor has been destructively tested by allowing it to dry out. Upon failure, the sensor current fluctuated wildly at relatively high frequency reflecting the random variations of the wetted cathode surface. This distinctive sign of failure is very obvious and unmistakable to any observer.

In the basic $CO_2$ sensor design FIG. 2, the potential impressed on the sensor electrode (i.e., cathode 34) is equal to the bias voltage minus the anode potential drop and the drop across the exchange membrane. Any variation in the potential drop within the anode or the anion exchange membrane may result in a slight change in the cathode potential and a change in the sensor current which is not mediated through a rise or fall in th $CO_2$ partial pressure.

Figure 8:
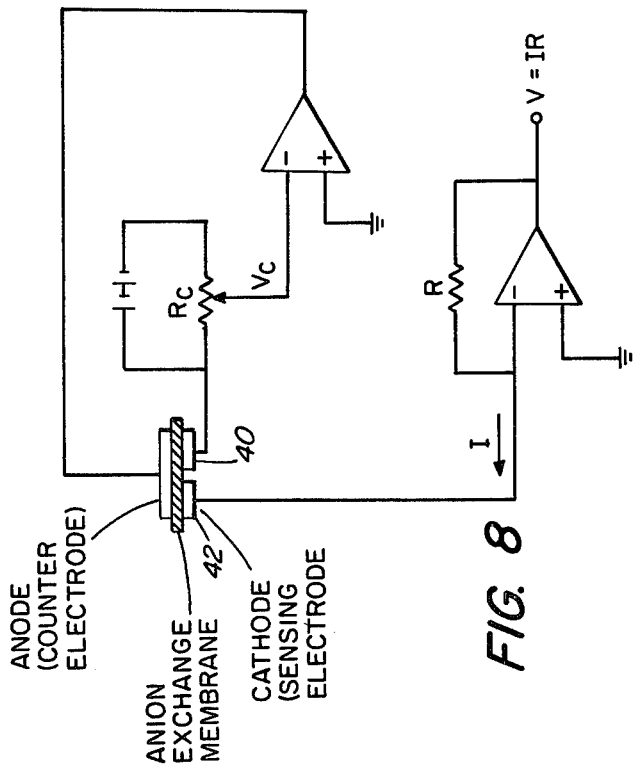

A constant cathodic bias unaffected by the anode or exchange membrane condition can be achieved by the addition of a third reference eletrode. Referring to FIG. 8 a reference electrode 40 is identical to the cathode of FIG. 2 with the exception that it is not polarized and no current (practically speaking) can flow through it. Through the feedback action of the operational ampifiers used, as shown the voltage between a sensing cathode 42 and the reference electrode 40 is always equal to the constant voltage V, irrespective of the condition and voltage drop of the anode or the anion exchange membrane.

The oxygen sensitivity of the $CO_2$ sensor can be reduced through judicious selection of the diffusion membrane material and the cathode material.

The offset current is reduced when the three-electrode design is implemented. The offset current does not appear to be a factor of concern. The service life of $CO_2$ sensor can be lengthened through judicious selection of a less permeable diffusion membrane.

The response time of the $CO_2$ sensor can be substantially reduced by using a very thin diffusion membrane (such as a Teflon membrane $8 \times 10^{-6}$ m in thickness).

Other modification to my inventive sensor will be apparent to those skilled in the art and are within the scope of the invention.

Having described my invention what I now claim is:

1. A method for measuring carbon dioxide which includes:
   placing a first diffusion membrane in communication with a fluid medium, the medium containing the carbon dioxide to be measured;
   flowing the carbon dioxide through the first diffusion membrane, the diffusion membrane permeation selective for carbon dioxide;
   hydrating said carbon dioxide to form anions and cations;
   flowing the anions through an anion exchange membrane;
   reforming the carbon dioxide at the anode;
   creating an electrolyte flow path between the anode and the cathode and through the electrolyte; and,
   measuring the current between the anode and the cathode to determine the level of selected species in the gaseous stream.

2. The method of claim 1 wherein the fluid medium is a gas.

3. The medium of claim 1 wherein the fluid medium is a liquid.

4. An electrolyte anion exchange sensor which comprises:
   a first diffusion membrane;
   an anion exchange membrane spaced apart from the first diffusion membrane and defining a cathodic compartment therebetween, the compartment containing electrolyte and a cathode;
   a second diffusion membrane spaced apart from the anion exchange membrane and defining therebetween an anodic compartment, the compartment having electrolyte disposed therein and including an anode;
   the first diffusion membrane adapted to pass therethrough carbon dioxide to be measured, the electrolyte adapted to hydrate said carbon dioxide to form anions and cations, the anion exchange membrane adapted to pass therethrough the anions formed in the cathodic compartment, said anions reacting at the anode in the anodic compartment to form carbon dioxide;
   means to form an electrolyte path between the anode and the cathode; and,
   means to measure the current which corresponds to the diffusion flux of the carbon dioxide to be measured.

5. The sensor of claim 4 wherein the first diffusion membrane is permeation selective for carbon dioxide and the anion exchange membrane is permeation selective for bicarbonate ions.

6. The sensor of claim 4 wherein the electrolyte is an enzyme based electrolyte adapted to hydrate the carbon dioxide to bicarbonate ions and hydrogen ions.

7. The sensor of claim 6 wherein the enzyme is carbonic anhydrase enzyme.

8. The sensor of claim 4 wherein the cathode is selected from the group consisting of gold-black, tantalum, cadmium, nickel, chromium and tungsten.

9. The sensor of claim 4 wherein the cathode and anode are each porous gold-black.

10. The sensor of claim 4 wherein the cathode in the cathodic compartment is a sensing cathode and which includes a second cathodic compartment having a gas diffusion membrane spaced apart from the anion exchange membrane and defining therebetween a cell having electrolyte and a reference cathode disposed therein; and, the means to form the electrolyte path includes means to maintain the voltage between the sensing cathode and the reference cathode equal.

* * * * *